United States Patent [19]
Folkman et al.

[11] Patent Number: 6,086,865
[45] Date of Patent: Jul. 11, 2000

[54] METHODS OF TREATING ANGIOGENESIS-INDUCED DISEASES AND PHARMACEUTICAL COMPOSITIONS THEREOF

[75] Inventors: Moses Judah Folkman; Harold Brem, both of Brookline, Mass.

[73] Assignee: Children's Medical Center Corporation, Boston, Mass.

[21] Appl. No.: 08/456,280

[22] Filed: May 31, 1995

Related U.S. Application Data

[63] Continuation of application No. 08/259,145, Jun. 13, 1994, abandoned, which is a continuation of application No. 07/832,854, Feb. 7, 1992, abandoned.

[51] Int. Cl.$^7$ .................... A61K 38/19; A61K 31/335
[52] U.S. Cl. .................. 424/85.1; 424/85.6; 424/85.7
[58] Field of Search ................... 424/85.4, 85.7, 424/85.1, 85.6; 514/2, 8, 24, 54, 58, 59, 475; 530/350, 395, 868

[56] References Cited

U.S. PATENT DOCUMENTS

| | | | |
|---|---|---|---|
| 5,019,562 | 5/1991 | Folkman et al. | 514/58 |
| 5,135,919 | 8/1992 | Folkman et al. | 514/56 |

FOREIGN PATENT DOCUMENTS

| | | |
|---|---|---|
| 0325199A1 | 7/1989 | European Pat. Off. . |
| 0357061A1 | 3/1990 | European Pat. Off. . |

OTHER PUBLICATIONS

Paul, W.F. (ed), *Fundamental Immunology* pp. 647–651. (1989) Raven Press, N.Y.
D. Ingber, et al. Nature 348: 555–557, Dec. 6, 1990.
Folkman, et al., *New England J. Med.*, 320:1211 (1989).
Ezekawitz, et al., *New England J. Med.*, 324:1456 (1992).
Folkman and Ingber, *Ann. Surg.*, 206:374–383 (1987).
Folkman, *Ann. Int. Med.*, 82:96–100 (1975).
Folkman, et al., *Nature*, 339:58–61 (1989).
Folkman, *J. Natn. Cancer Inst.*, 82:4–6 (1990).
Peacock, et al., *J. Exp. Med.*, 175:1135 (1992).
Brem, et al., *Surg. Forum*, 42:439 (1991).
S. Taylor, et al., Nature, 297:307 (1982).
M.J. Folkman, et al., Science, 221:719 (1983).
Japanese Kokai Tokkyo Koho No. 58–131978—Derwent Abstract.
Japanese Kokai Tokkyo Koho No. 63–119500—Derwent Abstract.
L. Liotta, Cancer Res. 34:997–1004 (1976).
M.J. Folkman, et al., Origins of Human Cancer: A Comprehensive Review, Cold Spring Harbor Laboratory Press, pp. 803–812 (1991).
Y. Sidky, et al., Cancer Research, 47:5155–5161 (1987).
C. White, et al., New England J. Med., 320:1197–1200 (1989).

*Primary Examiner*—Thomas M. Cunningham
*Attorney, Agent, or Firm*—Dike, Bronstein, Roberts & Cushman, LLP; David G. Conlin

[57] ABSTRACT

The present invention provides for the use of fumagillin or an O-substituted fumagillol derivative in conjunction with interferon which increases the angiogenic inhibitory action as compared with the agents administered alone. It has also been discovered that in the treatment of certain angiogenesis-induced diseases, the combination of the present invention is synergistic in angiogenesis inhibitory effect. The invention further provides a method for treatment of angiogenesis-induced diseases.

9 Claims, 4 Drawing Sheets

METHODS OF TREATING ANGIOGENESIS-INDUCED DISEASES AND PHARMACEUTICAL COMPOSITIONS THEREOF

This is a continuation of application(s) Ser. No. 08/259,145 filed on Jun. 13, 1994 (abandoned) which is a continuation of Ser. No. 07/832,854 filed on Feb. 7, 1992 (abandoned).

FIELD OF THE INVENTION

The present invention relates to combinations of angiogenesis inhibitors for the treatment and prevention of angiogenesis-induced diseases.

BACKGROUND OF THE INVENTION

Angiogenesis, the proliferation of new blood vessel growth, is involved in the manifestation or progress of various diseases, for example, various inflammatory diseases (rheumatism, psoriasis), diabetic retinopathy, and cancer.

Therefore, to inhibit angiogenesis is considered to contribute to the treatment and prevention of such diseases. In fact, several groups of researchers have so far searched for angiogenesis inhibitory substances. As examples, there may be mentioned the study by Taylor, et al., [S. Taylor, et al., *Nature*, 297:307 (1982)] on the applicability of protamine and the study of Folkman, et al. [M. J. Folkman, et al., *Science*, 221:719 (1983)] on the combined use of heparin and cortisone. Furthermore, patent applications have been filed alleging, for example, that ascorbic acid ethers and related compounds (Japanese Kokai Tokkyo Koho No. 58-131978) and the sulfated polysaccharide DS4152 (Japanese Kokai Tokkyo Koho No. 63-119500) show angiogenesis inhibitory activity.

One particular troubling angiogenesis-induced disease is tumor growth and metastasis. The ability of a tumor to metastasize depends on its ability to stimulate angiogenesis in at least two time-points in its growth; first, a tumor must be vascularized in order to enter circulation [L. Liotta, *Cancer Res.*, 34:997–1004 (1976)]; second, once it reaches the secondary site, the tumor must stimulate angiogenesis in order to expand [M. J. Folkman, *Origins of Human Cancer: A Comprehensive Review*, Cold Spring Harbor Laboratory Press, pp. 803–812 (1991)]. Other angiogenesis-induced diseases which present a problem to the medical community include rheumatoid arthritis, psoriasis and ocular angiogenic diseases including diabetic retinopathy.

Another group of angiogenesis inhibitors are fumagillin and O-substituted fumagillol derivatives such as those described in EPO Publication No. 0325199A2 and EPO Publication No. 0357061A1. The latter EPO Publication discloses O-substituted fumagillol derivatives of the general Formula I:

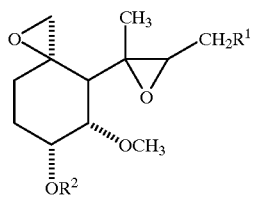

wherein $R^1$ is a 2-methyl-1-propenyl or isobutyl group which may be substituted and $R^2$ is (1) a substituted alkanoyl group, (2) a substituted aroyl group having at least one substituent selected from the group consisting of $C_{2-6}$ alkyl, amino, halogen, hydroxyl, lower alkoxyl, cyano, carbamoyl and carboxyl, (3) an aromatic heterocyclic-carbonyl which may optionally be substituted, (4) a carbamoyl group, which may optionally be substituted, (5) an alkyl group, which may optionally be substituted, (6) a benzenesulfonyl group, which may optionally be substituted, (7) an alkylsulfonyl group, which may be optionally substituted, (8) a sulfamoyl group, which may optionally be substituted, (9) an alkoxycarbonyl group, which may optionally be substituted or (10) a phenoxycarbonyl group which may optionally be substituted, or salts thereof.

Other inhibitors of angiogenesis include the lymphokine interferon. For example, interferon α/A or human interferon β has been shown to inhibit tumor-induced angiogenesis in mouse dermis stimulated by human neoplastic cells. [Y. Sidky, et al., *Cancer Research*, 47:5155:5161 (1987)] Likewise, interferon β is also a potent inhibitor of angiogenesis induced by allogeneic spleen cells. [Y. Sidky, et al., *Cancer Research*, supra] Human recombinant α interferon (α2A) was reported to be successfully used in the treatment of pulmonary hemangiomatosis, an angiogenesis-induced disease. [C. White, et al., *New England J. Med.*, 320:1197–1200 (1989)] However, interferon has only been shown to exhibit a relatively minor angiogenesis inhibitory effect and thus, interferon is only mildly effective in the treatment of angiogenesis induced diseases.

Accordingly, it would be desirable to have agents or novel combinations of agents which improve the inhibition of angiogenesis and thus the treatment of angiogenesis-induced diseases.

SUMMARY OF THE INVENTION

The present inventors have investigated the angiogenesis inhibitory action of a large number of combinations of anti-angiogenic agents in an attempt to find combinations with increased angiogenesis inhibitory action. The present inventors have discovered that most of the combinations tested did not provide an increased effect over the effect provided by the individual components when administered alone.

In accordance with the present invention, it has now been discovered that the use of fumagillin or an O-substituted fumagillol derivative in conjunction with interferon increases the angiogenic inhibitory action as compared with the agents administered alone. Moreover, it has also been discovered that in the treatment of certain angiogenesis-induced diseases, the combination of the present invention is synergistic in angiogenesis inhibitory effect.

According to a first feature of the present invention, there is provided a combination of (a) fumagillin or an O-substituted fumagillol derivative, and (b) an interferon, components (a) and (b) of the combination being employed in a ratio whereby an increased angiogenesis inhibitory effect is achieved.

In a second feature of the invention, there is provided the use of a combination as described above in the manufacture of a medicament for the treatment of angiogenesis-induced diseases. The invention further provides a method for inhibiting or preventing angiogenesis in mammals, for example, in the treatment of angiogenesis-induced diseases in a human or animal body which comprises administering to the human or animal body an effective amount of a combination as defined above. Such angiogenesis-induced diseases include solid tumors and tumor metastasis; benign tumors, for example, hemangiomas, acoustic neuromas, neurofibromas, trachomas, and pyogenic granulomas; rheumatoid arthritis; psoriasis; ocular angiogenic diseases, for example, diabetic retinopathy, retinopathy of prematurity, macular degeneration, corneal graft rejection, neovascular glaucoma, retrolental fibroplasia; and Osler-Webber Syndrome. The combination of the present invention may also be useful in the treatment of diseases of excessive or abnormal stimulation of endothelial cells, smooth muscle cells or fibroblasts. These diseases include intestinal adhesions, atherosclerosis, scleroderma, and hypertrophic scars, i.e., keloids. It will be appreciated then in accordance with the present invention that the fumagillin or O-substituted fumagillol derivative and the interferon may be administered simultaneously or sequentially, or even by different routes.

BRIEF DESCRIPTION OF THE DRAWINGS

FIG. 1 illustrates the T/C ratio versus days of treatment.
▼ IFN α/β (I.P.)
■ IFN α/β (I.T.)
● AGM-1470
▽ AGM-1470+IFN α/β (I.P.)
□ AGM-1470+IFN α/β (I.T.)

FIG. 2 illustrates the tumor volume (mm$^2$) after day 20 of treatment.

FIG. 3 illustrates the number of metastases present after 20 days of treatment.

FIG. 4 illustrates the percent increase in lung weight (lung weight correlates to tumor burden) after 20 days of treatment.

DETAILED DESCRIPTION OF THE INVENTION

Figure 1:
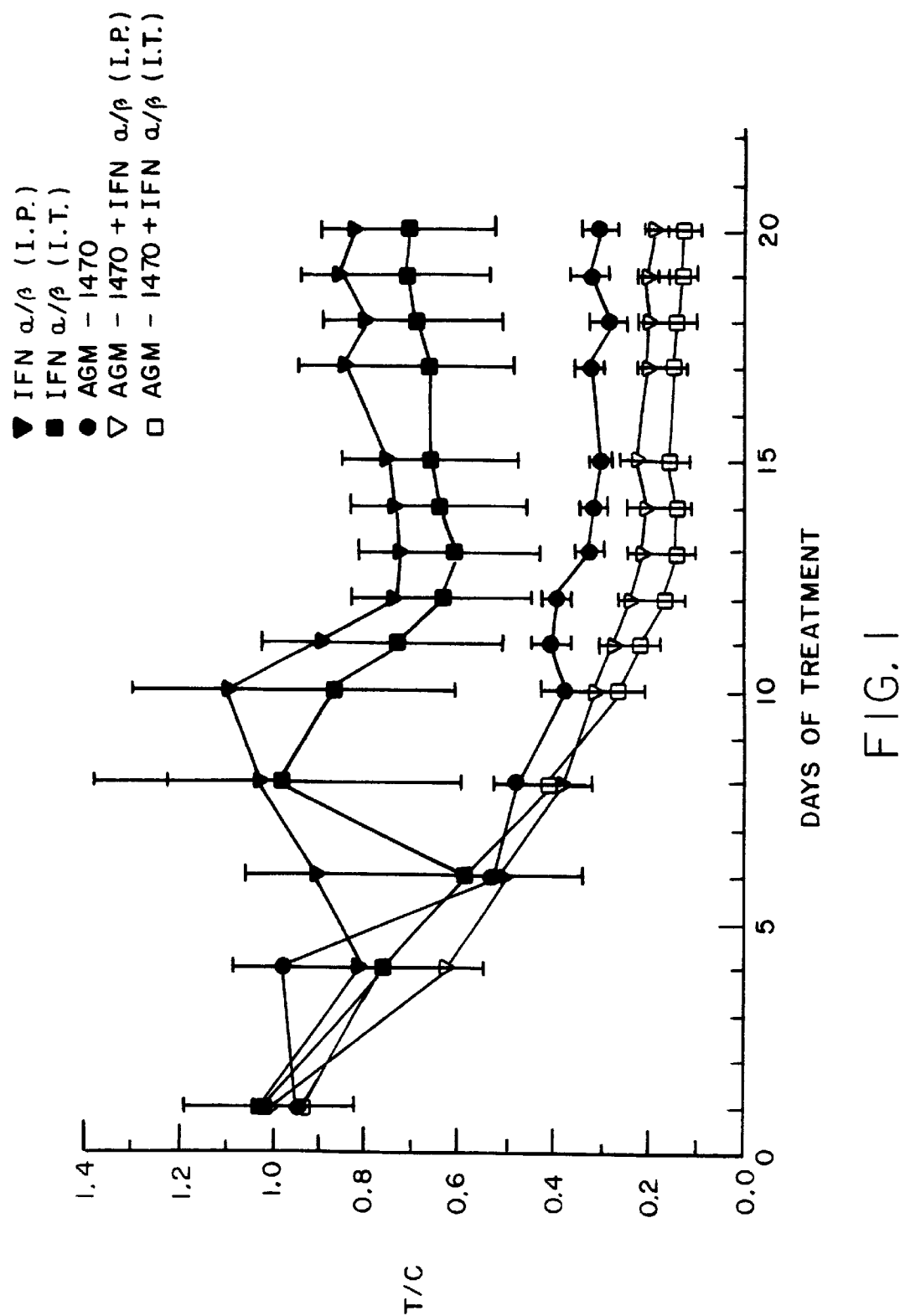
FIG. 1 through FIG. 4 show the results of treatment of Lewis Lung carcinoma with AGM-1470 and α/β interferon.
Figure 2:
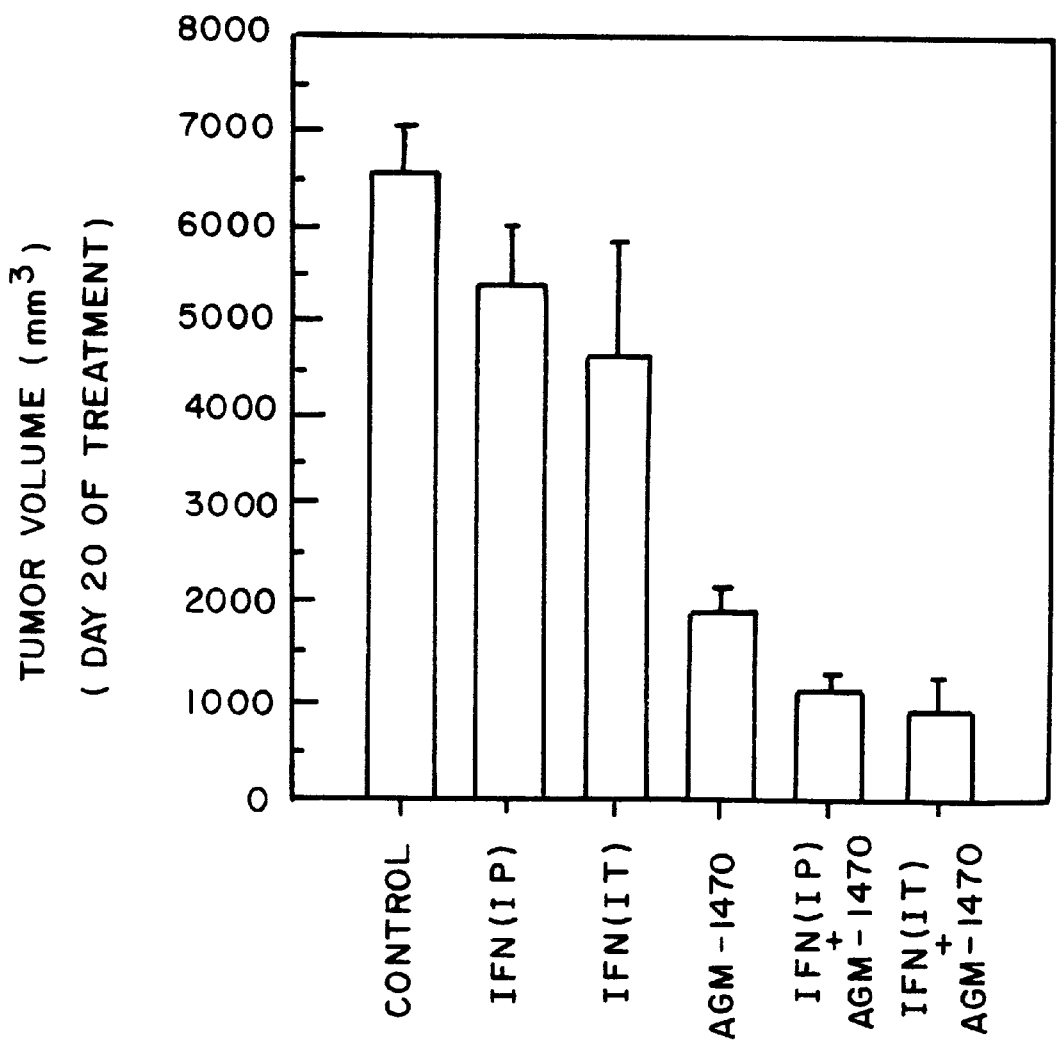
Figure 3:
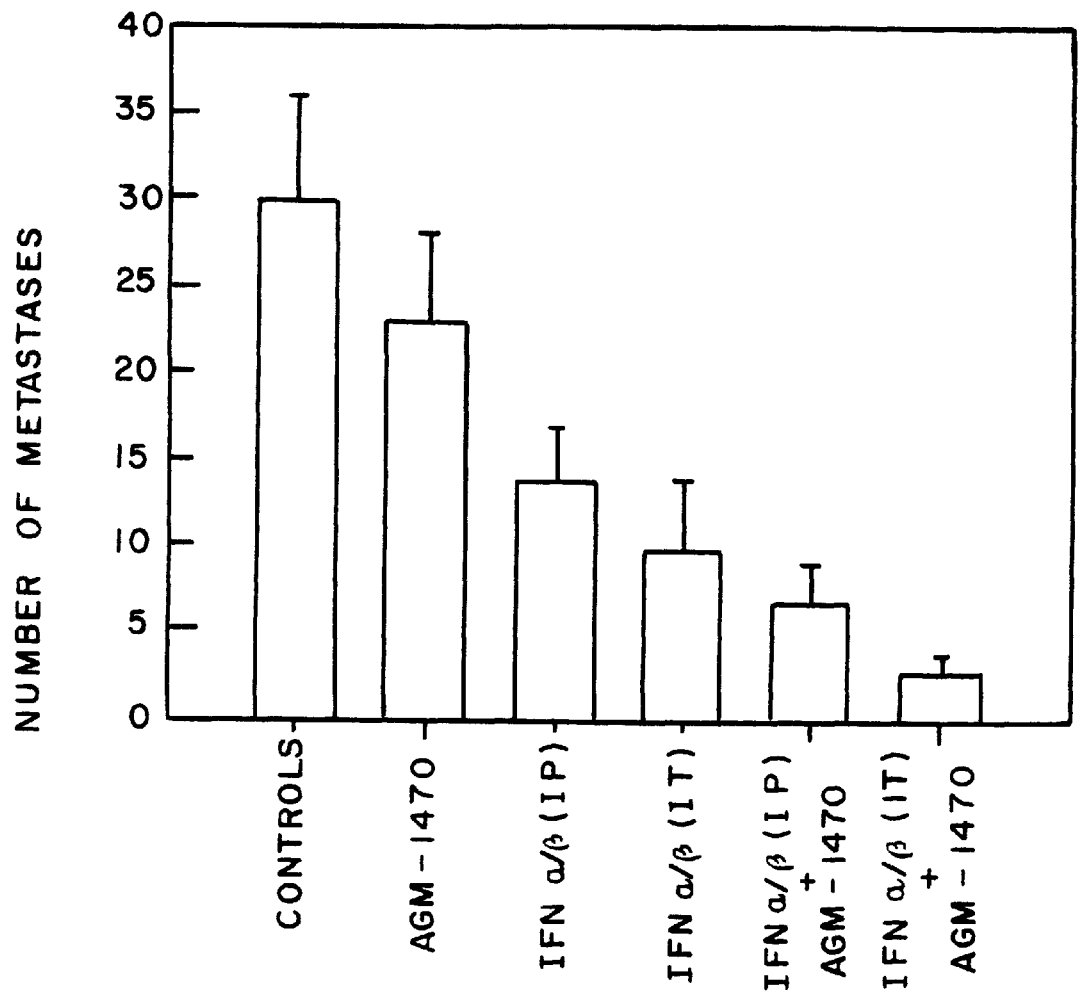
Figure 4:
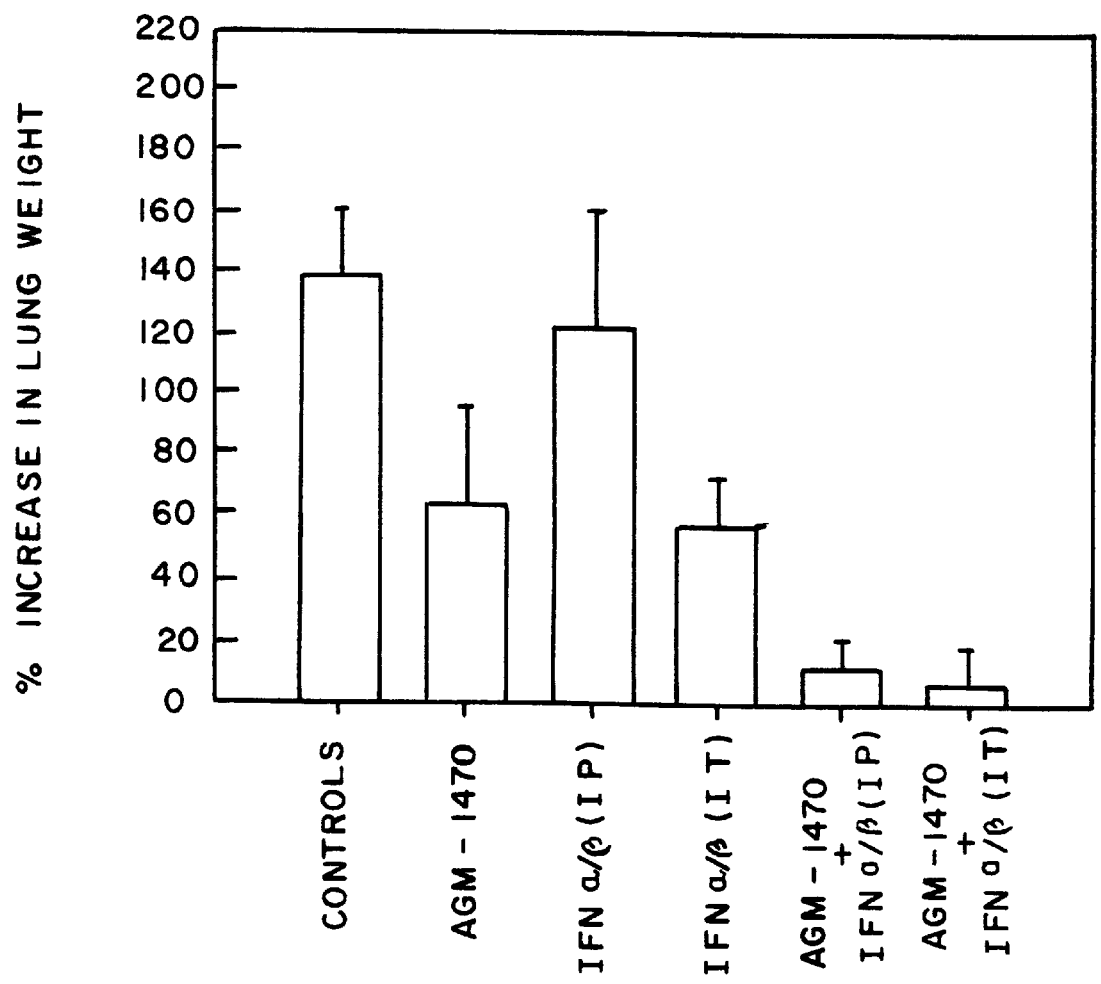

In accordance with the present invention, there is provided a combination of (a) fumagillin or an O-substituted fumagillol derivative, and (b) an interferon, components (a) and (b) of the combination being employed in a ratio whereby an increased angiogenesis inhibitory effect is achieved.

An advantage of the combination according to the present invention is that it enables one to obtain an increased anti-angiogenic efficacy by the combination of fumagillin or an O-substituted fumagillol derivative and interferon which is greater than when each is used alone.

With regard to the fumagillin compound, fumagillin disclosed in EPO Publication No. 0325199A2 may be used.

With regard to the fumagillol derivative compound, this may be selected from those compounds of Formula (I)

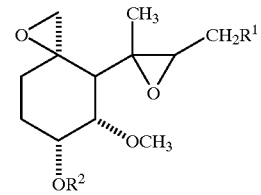
(I)

wherein R$^1$ is a 2-methyl-1-propenyl or isobutyl group which may be substituted and R$^2$ is (1) a substituted alkanoyl group, (2) a substituted aroyl group having at least one substituent selected from the group consisting of C$_{2-6}$ alkyl, amino, halogen, hydroxyl, lower alkoxyl, cyano, carbamoyl and carboxyl, (3) an aromatic heterocyclic-carbonyl which may optionally be substituted, (4) a carbamoyl group, which may optionally be substituted, (5) an alkyl group, which may optionally be substituted, (6) a benzenesulfonyl group, which may optionally be substituted, (7) an alkylsulfonyl group, which may be optionally substituted, (8) a sulfamoyl group, which may optionally be substituted, (9) an alkoxycarbonyl group, which may optionally be substituted or (10) a phenoxycarbonyl group which may optionally be substituted, or salts thereof.

The above described fumagillol derivatives are disclosed and can be obtained by the process described in European Patent Application No. 0357061A1, the disclosure of which is herein incorporated by reference.

The preferred compound of Formula (I) for use in accordance with the present invention is O-chloroacetylcarbamoylfumagillol (also referred to herein as AGM-1470) having a structure as follows:

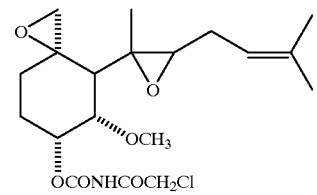

AGM-1470 can be prepared, for example, as follows: To a solution of fumagillol (314 mg) in dichloromethane (5 ml) was added dropwise chloroacetyl isocyanate (160 mg) under ice cooling, followed by addition of dimethylaminopyridine (130 mg). The mixture was stirred at 0° C. for 2 hours. To this reaction mixture was added water and the mixture was extracted with dichloromethane. The organic layer was washed with saturated aqueous sodium chloride solution and dried over anhydrous magnesium sulfate. The solvent was distilled off under reduced pressure and the residue was subjected to silica gel column chromatography. The eluate obtained using a mixture of n-hexane and ethyl acetate (3:1) was concentrated under reduced pressure to give colorless, powdery O-chloroacetylcarbamoylfumagillol (318 mg) (71% yield).

$^1$H-NMR (CDCl$_3$) δ: 1.10 (1H, m), 1.21 (3H, s), 1.66 (3H, s), 1.75 (3H, s), 1.93 (1H, d, J=11.4 Hz), 1.8–2.5 (5H, m), 2.57 (1H, d, J=4.2 Hz), 2.58 (1H, m), 2.99 (1H, d, J=4.2 Hz), 3.47 (3H, s), 3.68 (1H, dd, J=11.4 Hz, J=2.8 Hz), 4.44 (2H, s), 5.20 (1H, m), 5.61 (1H, m), 8.33 (1H, br s).

The interferons for use in accordance with the present invention may include leukocyte interferon (IFN-α), fibroblast interferon (IFN-β) and immune interferon (IFN-δ). The interferon may be isolated from natural sources or produced by recombinant DNA techniques. The interferons may include muteins as disclosed in U.S. Pat. No. 4,959,314, the disclosure of which is herein incorporated by reference. The interferons may also include hybrid interferon, such as those disclosed in U.S. Pat. Nos. 4,414,150 and 4,816,566, the disclosures of which are herein incorporated by reference. A large number of human and animal interferons are available from commercial suppliers. For example, human recombinant IFN-αA can be obtained from F. Hoffman-La Roche, Nutley, N.J.; human recombinant IFN $β_{Ser}$ can be obtained from Triton/Cetus, Alameda, Calif.; and IFN-γ is available from Genentech, San Francisco, Calif. Murine interferon, including INFα/β, rat interferons, rabbit interferons, as well as human interferons can be obtained from Lee Bromolecular, San Diego, Calif. The interferon used in the present invention is preferably specific for the species to be treated. For example, human IFN α would preferably be used in the treatment of humans.

The present invention may be accomplished by bringing into association the above-defined fumagillin or fumagillol derivatives and an interferon to provide an increased anti-angiogenesis effect. The combinations according to the invention may be administered to the subject concerned in a conventional manner. As indicated above, the fumagillol derivative and interferon may be administered simultaneously (in a unitary pharmaceutical formulation or administered simultaneously in a separate formulation or separately (e.g., in separate pharmaceutical formulations). If administered separately, the components may be provided in a kit, each component being provided as a separate pharmaceutical formulation. In general, the combinations may be administered by the topical, oral, rectal or parenteral (e.g., intravenous, subcutaneous or intramuscular) route. In addition, the combinations may be incorporated into biodegradable polymers allowing for sustained release, the polymers being implanted in the vicinity of where drug delivery is desired, for example, at the site of a tumor. The biodegradable polymers and their use are described in detail in H. Brem, et al., *J. Neurosurg.*, 74:441–446 (1991).

When fumagillol derivatives are used as the first component, the range ratios of the fumagillol derivative to the interferon is from 100:1 to 1:1000, preferably from 10:1 to 1:10. The dosage of the combination will depend on the condition being treated, the particular fumagillol derivative and interferon concerned and other clinical factors such as weight and condition of the patient and the route of administration of the compound. However, for administration by the oral route, a dosage of the fumagillol derivative of 1 to 600 mg/kg/day, preferably 10 to 100 mg/kg/day, is generally sufficient. For administration by the parenteral route, a dosage of fumagillol derivative of 1 to 100 mg/kg/day, preferably 10 to 30 mg/kg/day, is generally sufficient. The amount of interferon used in combination with the fumagillol derivative specified above is preferably in a range of 1,000 to $5 \times 10^8$ IU/m²/day, and particularly in a range of $0.2 \times 10^7$ to $2 \times 10^7$ IU/m²/day.

For example, when the fumagillol derivative is administered orally, the amount would range from 10 to 600 mg/kg/day and the amount of interferon administered orally would range from $1 \times 10^5$ to $1 \times 10^8$ IU/m²/day. When the fumagillol derivative is administered orally and the interferon is administered parenterally, the amount of the fumagillol derivative would range from 10 to 600 mg/kg/day and the amount of interferon would range from $1 \times 10^5$ to $1 \times 10^8$ IU/m²/day. When both components are administered parenterally, the amount of fumagillol derivative would range from preferably 10 to 30 mg/kg/day and the amount of interferon would range from $1 \times 10^5$ to $1 \times 10^8$ IU/m²/day. In addition, interferon, alone or in combination with the fumagillol derivative, may be administered intra-lesionally or topically, the dosage being in a range from $1 \times 10^5$ to $1 \times 10^8$ IU/m²/day.

For convenience, the fumagillol derivative and the interferon are preferably administered in a unitary pharmaceutical composition. Thus, the present invention further provides a pharmaceutical formulation comprising a fumagillol derivative as defined above in accordance with the invention, and an interferon, together with at least one pharmaceutical carrier or excipient, the fumagillol derivative and interferon being present in the formulation in a ratio, whereby an increased anti-angiogenesis effect is achieved upon administration to a human or animal subject.

The formulations include those suitable for oral, rectal, nasal, topical (including buccal and sublingual), vaginal or parenteral (including subcutaneous, intramuscular, intravenous, intradermal, intratracheal, and epidural) administration. The formulations may conveniently be presented in unit dosage form and may be prepared by conventional pharmaceutical techniques. Such techniques include the step of bringing into association the active ingredients for the pharmaceutical carrier(s) or excipient(s). In general, the formulations are prepared by uniformly and intimately bringing intimately bringing into associate the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil emulsion and as a bolus, etc.

A tablet may be made by compression or molding, optionally with one or more accessory ingredients. Compressed tablets may be prepared by compressing, in a suitable machine, the active ingredient in a free-flowing form such as a powder or granules, optionally mixed with a binder, lubricant, inert diluent, preservative, surface-active or dispersing agent. Molded tablets may be made by molding, in a suitable machine, a mixture of the powdered compound moistened with an inert liquid diluent. The tablets may optionally coated or scored and may be formulated so as to provide a slow or controlled release of the active ingredient therein.

Formulations suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin may be presented as ointments, creams, gels and pastes comprising the ingredient to be administered in a pharmaceutical acceptable carrier. A preferred topical delivery system is a transdermal patch containing the ingredient to be administered.

Formulations for rectal administration may be presented as a suppository with a suitable base comprising, for example, cocoa butter or a salicylate.

Formulations suitable for nasal administration, wherein the carrier is a solid, include a coarse powder having a particle size, for example, in the range of 20 to 500 microns which is administered in the manner in which snuff is taken, i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

Formulations suitable for vaginal administration may be presented as pessaries, tampons, creams, gels, pastes, foams or spray formulations containing in addition to the active ingredient such as carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) conditions requiring only the addition of the sterile liquid carrier, for example, water for injections, immediately prior to use. Extemporaneous injection solutions and suspensions may be prepared from sterile powders, granules and tables of the kind previously described.

Preferred unit dosage formulations are those containing a daily dose or unit, daily sub-dose, as herein above recited, or an appropriate fraction thereof, of the administered ingredient.

It should be understood that in addition to the ingredients, particularly mentioned above, the formulations of this invention may include other agents convention in the art having regard to the type of formulation in question, for example, those suitable for oral administration may include flavoring agents.

The Example below demonstrates the ability of the combination of the present invention in the treatment of tumors including the inhibition or suppression of metastasis. In addition to treating primary tumor growth and metastases, the combination of the present invention may be used in the treatment of a variety of diseases or angiogenesis as a primary component.

In the Example, set out below, the Lewis Lung carcinoma LI tumor cell line (LLC-L1) was used. This line was derived by passage of Lewis Lung carcinoma (courtesy of Arthur D. Little, Inc.) which was implanted subcutaneously and grown to a size of 3 grams. A lung metastasis was harvested, grown in culture and subsequently passed subcutaneously. This cell line has a higher affinity than the parent line for seeding in the lung.

By the following Example, the present invention will be described in more detail, but the present invention is by no means limited to this Example.

EXAMPLE I

Anti-Tumor Effect of the Combination of AGM-1470 and α/β Interferon Against Solid Tumors (LLC-L1) and Tumor Metastases $1 \times 10^6$ Lewis Lung carcinoma cells (LLC-L1) were injected subcutaneously until a solid tumor had formed on the dorsum, i.e., on the back of a C57/B1/6 mouse. Three days later, solid tumors had formed averaging 108 $mm^3$. Treatment then began and continued for 20 days. There were four to eight mice per group, divided into the following groups:

Group A: AGM-1470, 30 mg/kg subcutaneously at a site distal or remote from the tumor plus α/β interferon, 800,000 units injected per day into the peritoneum;

Group B: AGM-1470, 30 mg/kg subcutaneously at a site distal or remote from the tumor plus α/β interferon, 800,000 units per day intra-tumorally;

Group C: AGM-1470, 30 mg/kg subcutaneously at a site distal or remote from the tumor;

Group D: α/β interferon, 800,000 units per day intra-tumorally;

Group E: α/β interferon, 800,000 units per day in the peritoneum; and

Group F: Control mice=saline injected subcutaneously every other day (0.3 cc/20 g).

AGM-1470 was generously provided by Takeda Chemical Industries, Ltd., Osaka, Japan; α/β interferon was generously provided by Dr. Ion Gresser, Laboratory of Virology and Cancer, Villejuif, France.

The results are presented in FIGS. 5–8. In the Figures, IP stands for intra-peritoneum, IT=intratumor.

Statistical significance is presented below in Table 1.

There was no weight loss in any of the groups of mice with any of these drugs alone or in combination.

TABLE 1

| Day 20 Tumor Volume t-test (independent) | | | |
|---|---|---|---|
| Group | t | p | .05 Confidence |
| AGM-1470 vs Control | 9.655 | $2.695 \times 10^{-5}$ | Different |
| IFN (ip) + AGM-1470 | | | |
| vs Control | $1.472 \times 10$ | $1.328 \times 10^{-7}$ | Different |
| vs AGM | 3.117 | $1.093 \times 10^{-2}$ | Different |
| vs IFN (ip) | 8.008 | $1.167 \times 10^{-5}$ | Different |
| vs IFN (it) + AGM | $-7.468 \times 10^{-1}$ | $4.724 \times 10^{-1}$ | Not Different |
| IFN (it) + AGM-1470 | | | |
| vs Control | $1.065 \times 10$ | $1.414 \times 10^{-5}$ | Different |
| vs AGM | $-2.560$ | $3.364 \times 10^{-2}$ | Different |
| vs IFN (it) | 3.243 | $1.4187 \times 10^{-2}$ | Different |
| vs IFN (ip) + AGM | $-7.468 \times 10^{-1}$ | $4.724 \times 10^{-1}$ | Not Different |
| Control | | | |
| vs IFN (ip) | 1.461 | $1.873 \times 10^{-1}$ | Not Different |
| vs IFN (it) | 1.487 | $1.874 \times 10^{-1}$ | Not Different |
| IFN (ip) vs IFN (it) | $6.082 \times 10^{-1}$ | $5.622 \times 10^{-1}$ | Not Different |

What is claimed is:

1. A pharmaceutical formulation comprising (a) a first component, O-chloracetylcarbamoylfumagillol, and (b) a second component comprising interferon, the amount of each component being present in amounts which provide an increased angiogenesis inhibitory effect, wherein the interferon is selected from the group consisting of human interferon α and human interferon β.

2. The pharmaceutical composition of claim 1, wherein the the interferon is human interferon α.

3. The pharmaceutical formulation of claim 1, wherein the ratio of O-chloroacetylcarbamoylfumagillol to interferon is about 100:1 by weight up to about 1:1000 by weight.

4. A kit comprising a pharmaceutical formulation comprising O-chloroacetylcarbamoylfumagillol and a pharmaceutical formulation comprising interferon, wherein the interferon is selected from the group consisting of human interferon α and human interferon β.

5. A method for inhibiting angiogenesis in a mammal comprising, administering to said mammal an effective amount of a pharmaceutical formulation comprising (a) a first component, O-chloroacetylcarbamoylfumagillol, and (b) a second component comprising interferon, the amount of each component being present in amounts which provide increased angiogenesis inhibitory effect, wherein the interferon is selected from the group consisting of human interferon α and human interferon β.

6. A method of inhibiting angiogenesis in a mammal comprising, administering to said mammal (a) a first component comprising a pharmaceutical composition O-chloroacetylcarbamoylfumagillol, and (b) a second component comprising a pharmaceutical composition of interferon, each component being administered in an amount which provides an increased angiogenesis inhibitory effect, wherein the interferon is selected from the group consisting of human interferon α and human interferon β.

7. The method of claim 6, wherein components (a) and (b) are administered simultaneously.

8. The method of claim 6, wherein components (a) and (b) are administered sequentially.

9. The method of claim 6, wherein components (a) and (b) are administered via different routes.

* * * * *